United States Patent [19]

Chang et al.

[11] Patent Number: 5,607,888
[45] Date of Patent: Mar. 4, 1997

[54] REGIOSELECTIVE METHYLATION OF TOLUENE TO PARA-XYLENE

[75] Inventors: Clarence D. Chang, Princeton; Paul G. Rodewald, Rocky Hill, both of N.J.

[73] Assignee: Mobil Oil Corporation, Fairfax, Va.

[21] Appl. No.: 452,939

[22] Filed: May 30, 1995

Related U.S. Application Data

[62] Division of Ser. No. 223,383, Apr. 5, 1994, Pat. No. 5,498,814, which is a continuation of Ser. No. 24,972, Mar. 2, 1993, abandoned, which is a continuation-in-part of Ser. No. 850,105, Mar. 12, 1992, abandoned.

[51] Int. Cl.$^6$ .................................................. B01J 29/06
[52] U.S. Cl. .................................. 502/64; 502/63; 502/71
[58] Field of Search ................................... 502/63, 64, 71

[56] References Cited

U.S. PATENT DOCUMENTS

| | | | |
|---|---|---|---|
| 3,682,996 | 8/1972 | Kerr | 260/448.8 R |
| 3,698,157 | 10/1972 | Allen et al. | 55/67 |
| 4,090,981 | 5/1978 | Rodewald | 252/455 Z |
| 4,100,215 | 7/1978 | Chen | 260/671 M |
| 4,127,616 | 11/1978 | Rodewald | 260/671 R |
| 4,477,583 | 10/1984 | Rodewald | 502/71 |
| 4,950,835 | 8/1990 | Wang et al. | 585/467 |
| 5,382,737 | 1/1995 | Beck et al. | 585/475 |

*Primary Examiner*—Gary P. Straub
*Assistant Examiner*—Thomas G. Dunn, Jr.
*Attorney, Agent, or Firm*—Malcolm D. Keen; Peter W. Roberts

[57] ABSTRACT

A process and catalyst for Shape Selective Hydrocarbon Conversions such as the regioselective disproportionation of toluene to para-xylene wherein hydrocarbon to be converted is passed over a catalytic molecular sieve which is trim selectivated with a reaction stream comprising toluene and a silicon-containing high efficiency p-xylene selectivating agent under toluene conversion conditions. The toluene disproportionation process attains a single-pass para-xylene product over 95% coupled with a toluene conversion of at least 15%. The present invention also includes the highly para-selective catalyst which results from the treatment of a catalytic molecular sieve with a high efficiency p-xylene selectivating agent under the recited conditions.

7 Claims, 4 Drawing Sheets

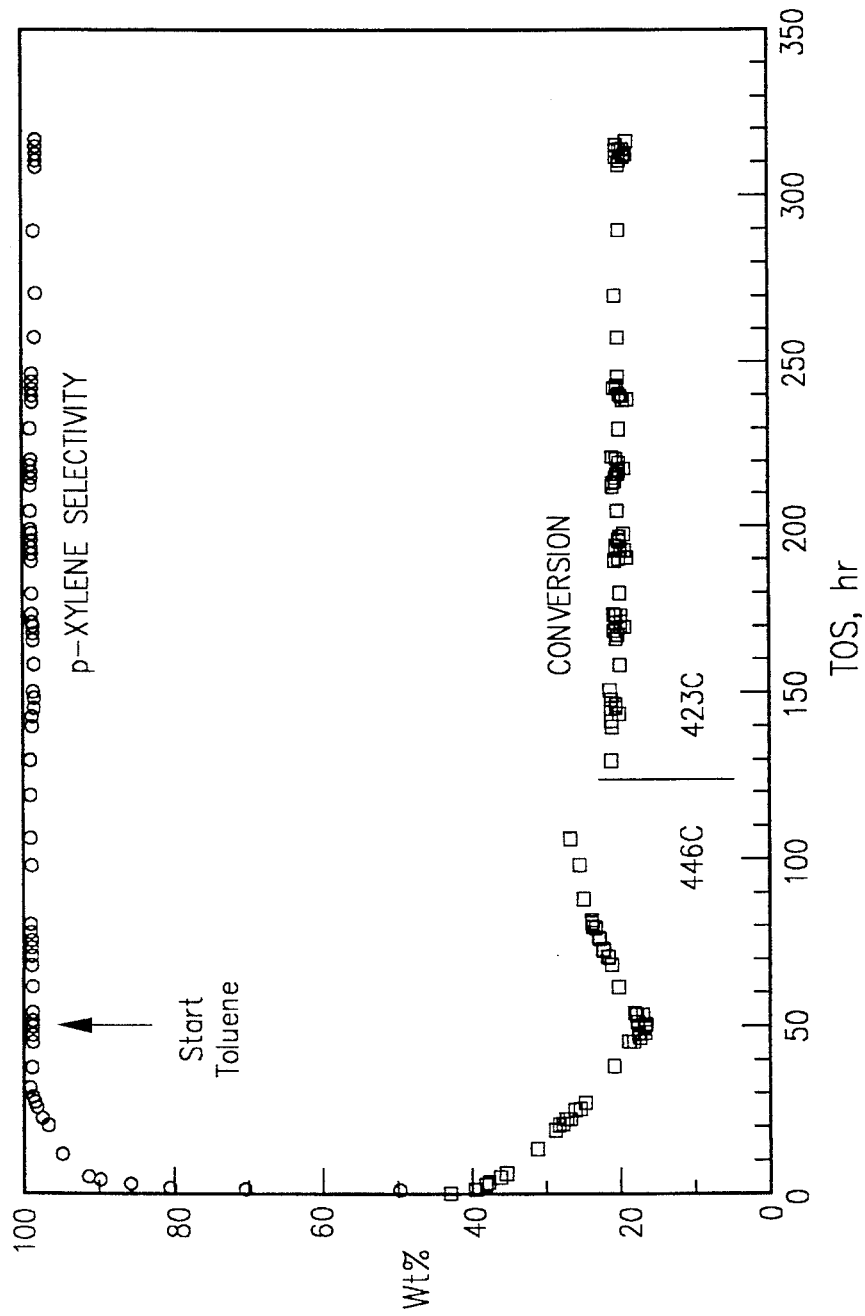

REGIOSELECTIVE METHYLATION OF TOLUENE TO PARA-XYLENE

CROSS REFERENCE TO RELATED APPLICATION

This application is a division of copending U.S. application Ser. No. 08/223,383, filed Apr. 5, 1994, now U.S. Pat. No. 5,498,814, which is a continuation of copending U.S. application Ser. No. 08/024,972, filed Mar. 2, 1993, now abandoned, which is a continuation-in-part of copending U.S. application Ser. No. 07/850,105 filed Mar. 12, 1992, now abandoned.

BACKGROUND

The present invention is directed to a process and catalyst for shape selective hydrocarbon conversions such as the regioselective conversion of toluene to para-xylene.

The term shape-selective catalysis describes unexpected catalytic selectivities in zeolites. The principles behind shape selective catalysis have been reviewed extensively, e.g. by N. Y. Chen, W. E. Garwood and F. G. Dwyer, "Shape Selective Catalysis in Industrial Applications," 36, Marcel Dekker, Inc. 1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational diffusion where the dimensions of the molecule approach that of the zeolite pore system. A small change in dimensions of the molecule or the zeolite pore can result in large diffusion changes leading to different product distributions. This type of shape selective catalysis is demonstrated, for example, in toluene selective disproportionation to p-xylene.

Para-xylene is a very valuable commercial product useful in the production of polyester fibers. The catalytic production of para-xylene has received much attention in the scientific community and various methods for increasing catalyst para-selectivity have been described.

The synthesis of para-xylene is typically performed by methylation of toluene over a catalyst under conversion conditions. Examples are the reaction of toluene with methanol as described by Chen et al., J. Amer. Chem. Sec. 1979, 101, 6783, and toluene disproportionation, as described by Pines in "The Chemistry of Catalytic Hydrocarbon Conversions", Academic Press, N.Y., 1981, p. 72. Such methods typically result in the production of a mixture including para-xylene, ortho-xylene, and meta-xylene. Depending upon the para-selectivity of the catalyst and the reaction conditions, different percentages of para-xylene are obtained. The yield, i.e., the amount of feedstock actually converted to xylene, is also affected by the catalyst and the reaction conditions.

The equilibrium reaction for the conversion of toluene to xylene and benzene proceeds as follows:

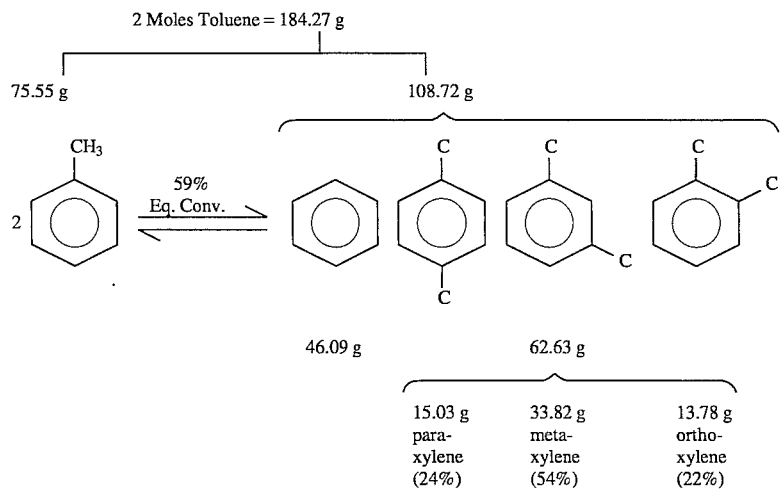

$$\text{p-Xylene Yield} = 100 \times \frac{15.03}{184.27} = 8.2\%$$

$$\text{Yield} = \text{Selectivity} \times \text{Conversion} = \frac{15.03}{108.72} \times 0.59 = 8.2\%$$

$$\text{p-Xylene purity} = 100 \times \frac{15.03}{62.63} = 24\%$$

One known method for increasing para-selectivity of zeolite catalysts is to modify the catalyst by treatment with "selectivating agents". Modification methods have been suggested wherein the catalyst is modified by treatment prior to use to provide a silica coating. For example, U.S. Pat. Nos. 4,477,583 and 4,127,616 disclose methods wherein a catalyst is contacted at ambient conditions with a modifying compound such as phenylmethyl silicone in a hydrocarbon solvent or an aqueous emulsion, followed by calcination. Such modification procedures have been successful in obtaining para-selectivity of greater than about 90% but with commercially unacceptable toluene conversions of only about 10%, resulting in a yield of not greater than about 9%, i.e. 10%×90%. Such processes also produce significant quantities of ortho-xylene and meta-xylene thereby necessitating expensive separation processes in order to separate the para-xylene from the other isomers.

Typical separation procedures include costly fractional crystallization and adsorptive separation of para-xylene from other xylene isomers which are customarily recycled. Xylene isomerization units are then required for additional conversion of the recycled xylene isomers into an equilibrium xylene mixture comprising para-xylene.

Those skilled in the art appreciate that the expense of the separation process is proportional to the degree of separation required. Therefore, significant cost savings are achieved by increasing selectivity to the para-isomer while maintaining commercially acceptable conversion levels.

It is, therefore, highly desirable to provide a regioselective process for the production of para-xylene from toluene while maintaining commercially acceptable toluene conversion levels.

SUMMARY OF THE INVENTION

One process of the present invention comprises the regioselective conversion of toluene to para-xylene by disproportionating toluene in a reaction stream containing a toluene feed with a catalytic molecular sieve under reaction conditions to provide a single pass, para-xylene product of at least about 90% based on the $C_8$ products.

The present invention also comprises a new regioselective disproportionation catalyst for the conversion of toluene to para-xylene formed by contacting a reaction stream which contains toluene in a single pass over a catalytic molecular sieve, in the presence of hydrogen, at reaction conditions suitable to provide a para-xylene purity of greater than about 95%. As used herein, the term "xylene product" indicates the total amount of xylenes resulting from the disproportionation reaction.

In one particular aspect of the present invention, toluene is contacted with a catalytic molecular sieve having a constraint index of about 1–20 at reaction conditions suitable for converting the toluene to xylene. In one embodiment of the present invention, the toluene is fed simultaneously with a high-efficiency selectivating agent and hydrogen at reaction conditions until the desired xylene p-selectivity, e.g., about 95%, is attained, whereupon the feed of selectivating agent is discontinued. This co-feeding of selectivating agent with toluene will hereinafter be termed "trim selectivation". Reaction conditions generally include a temperature of about 350°–540° C. and a pressure of about atmospheric—5000 psig. The feed is provided to the system at a rate of about 0.1–20 WHSV. The hydrogen is fed at a hydrogen to hydrocarbon molar ratio of about 0.1–20.

The high efficiency para-xylene selectivating agent preferably comprises an organosilicon compound, for example, organic polysiloxanes, silicones, siloxanes, silanes and mixtures thereof. According to one embodiment of the present invention, a silicone containing phenylmethylsilicon and dimethylsilicon groups in a ratio of about 1:1 is co-fed to the system, while the other components, e.g., toluene and hydrogen, are fed in the amounts set forth above. The high-efficiency para-xylene selectivating agent is fed in an amount of about 0.1%–50% of the toluene according to this preferred embodiment. Depending upon the percentage of selectivating agent used, the trim selectivation will preferably last for about 50–300 hours, most preferably less than 170 hours.

The processes disclosed herein greatly enhance the efficiency of para-xylene production. For example, a para-xylene purity of greater than 90%, preferably at least 95%, based on all $C_8$ products can be attained with a toluene conversion of greater than 15%, preferably at least 20%, and most preferably at least 25%. Processes of the prior art typically require expensive secondary and tertiary treatment procedures in order to obtain these efficiencies.

Consequently, the present invention provides unique reactions which significantly enhance para-selectivity. Moreover, the highly efficient conversion of the present invention can be carried out in a single pass of the reactant stream with a resulting product stream having reduced amounts of unwanted impurities and/or side products.

The invention is also a process for shape selective hydrocarbon conversions. A reaction stream comprising hydrocarbon to be converted is contacted with molecular sieve catalyst which has been trim selectivated. The shape selective hydrocarbon conversions include dewaxing of paraffins; isomerization of alkylaromatics, oligomerization of olefins, alkylating of aromatics, conversion of oxygenates to hydrocarbons and conversion of paraffins and olefins to aromatics.

BRIEF DESCRIPTION OF THE DRAWINGS

FIG. 4 is a graph showing para-xylene and toluene conversion as a function of time on stream.

DETAILED DESCRIPTION

Figure 1:
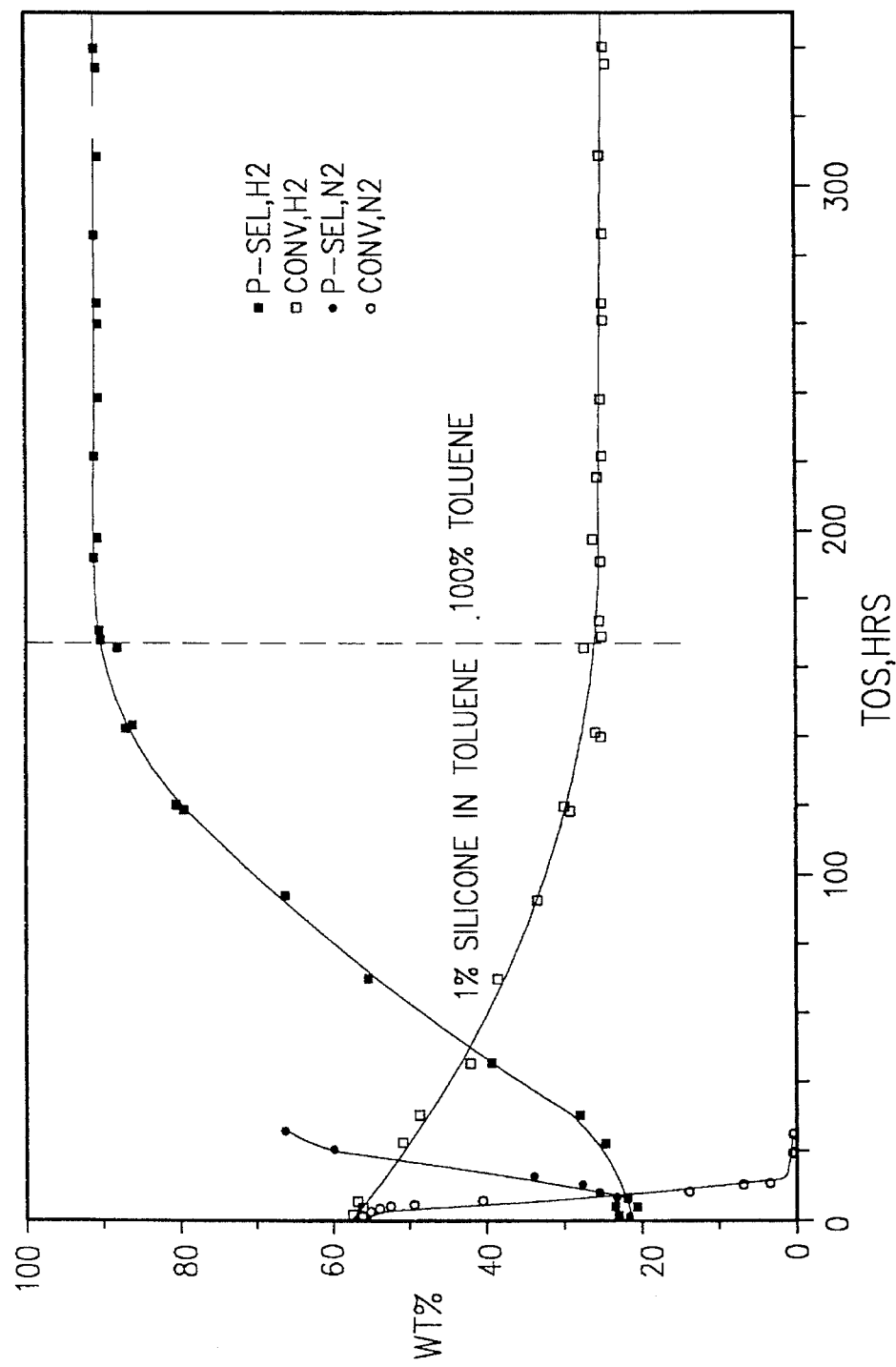
FIG. 1 is a graph comparing xylene para-selectivity and toluene conversion in the presence of hydrogen or nitrogen as a function of stream time.

The present invention is useful in Shape Selective hydrocarbon conversions.

SHAPE SELECTIVE CONVERSIONS

Zeolites modified in accordance with the invention are generally useful as catalysts in shape selective hydrocarbon conversion processes including cracking reactions involving dewaxing of hydrocarbon feedstocks; isomerization of alkylaromatics; oligomerization of olefins to form gasoline, distillate, lube oils or chemicals; alkylation of aromatics; conversion of oxygenates to hydrocarbons; rearrangement of oxygenates; and conversion of light paraffins and olefins to aromatics.

Dewaxing

The subject catalysts have good cracking and hydrocracking activity and may be used to convert paraffins from high to low molecular weight substances in dewaxing processes. The catalysts of the invention may be used in processes such as those described, for example, in U.S. Pat. Nos. 3,700,585, Re. 28,398, 3,968,024 and 4,181,598 which are incorporated herein by references. The term dewaxing means the removal of those hydrocarbons which will readily solidify (waxes) from petroleum stocks. Hydrocarbon feeds which can be treated include lubricating oil stocks as well as those which have a freeze point or pour point problem, i.e., petroleum stocks boiling above 350° F. The dewaxing cab be carried out at either cracking or hydrocracking conditions.

In U.S. Pat. No. 3,700,585 and Re. 28,398 to Chen et al., typical cracking conditions include a liquid hourly space velocity (LHSV) between about 0.5 and 200, a temperature between about 288° C. (550° F.) and 590° C. (1100° F.), a pressure between about subatmospheric and several hundred atmospheres over ZSM-5 type catalysts. Typical hydrocracking conditions include a liquid hourly space velocity between about 0.1 and 10, a temperature between about 340° C. (650° F.) and 538° (1000° F.), a pressure between about 100 and 3000 psig, and a hydrogen to hydrocarbon mole ratio between about one and 20. U.S. Pat. No. 3,968,024 describes similar conversions using ZSM-5 of small crystal size. U.S. Pat. No. 4,181,598 describes shape selective cracking to produce lubes.

Isomerization of alkylaromatics

The modified catalysts of the invention are also advantageously used in the isomerization of alkylaromatics in conversion reactions of the type described, for example, in U.S. Pat. Nos. 3,856,872, 3,856,873, Re. 30,157, 4,101,595, 4,101,597, 4,312,790, Re. 31,919 and 4,224,141 which are herein incorporated by reference.

In U.S. Pat. No. 3,856,872 to Morrison, there is described a process for converting $C_8$ aromatics xylene and ethylbenzene to para-xylene (octafining) at a temperature of 550° F. (288° C.) to 900° F. (482° C.), a pressure of 150 to 300 psig, and a liquid hour space velocity (LHSV) of 1 to 200 over an acid-form catalyst containing metal such as platinum or nickel and hydrogen.

In U.S. Pat. No. 3,856,873 to Burress, mixtures of $C_{8a}$ aromatic hydrocarbons are isomerized to para-xylene by contact in vapor phase with zeolite at a temperature of 500° F. (260° C.) to 1000° F. (538° C.), a pressure of 0 (atmospheric) to 1,000 psig, and a WHSV of 0.5 to 250 with no added hydrogen. The catalyst is an acid ZSM-5, ZSM-12 or ZSM-21.

U.S. Pat. No. 4,101,595 to Chen et al. describes the production of para-xylene from aromatics of 8 to 10 carbons over a dual function catalyst with a shape selective acid catalyzed step at a temperature of 650° F. (343° C.) to 1000° F. (538° C.), a pressure of 50 to 500 psig, a LHSV of 0.1 to 100 and a molar ratio of hydrogen/hydrocarbon of 0.1 to 15. The acid form catalyst has a Constraint Index of 1 to 12, a silica/alumina ratio of at least 12, a crystal density of not less than 1.6 g/cc, may be pre-coked, and includes Group VIII noble metal.

In U.S. Pat. No. 4,101,597 to Breckenridge, a $C_8$ feed is first isomerized at 550° F. (288° C.) to 700° F. (371° C.) over a zeolite having a Constraint Index of 1 to 12, a silica/alumina ratio of at least 12 and containing a metal having a hydrogenation/dehydrogenation function. A $C^{9+}$ fraction produced during isomerization of $C_8$ is separated from the other isomerization products, blended with hydrogen and toluene and contacted with a porous, acidic catalyst such as ZSM-5 at 750° F. (399° C.) to 900° F. (482° C.). The catalyst has a Constraint Index of 1 to 12, a silica/alumina ratio of at least 12, and a metal providing hydrogenation/dehydrogenation function.

In U.S. Pat. No. 4,224,141 to Morrison, $C_8$ aromatics are isomerized to benzene, toluene and xylenes over a ZSM-5 which is reduced in activity by dilution with inert matrix, steaming or thermal treatment, very high silica/alumina ratio, base exchange with alkali metal, coking or the like. The conversion is at a temperature of 800° F. (427° C.) to 1000° F. (538° C.) in a low pressure isomerization unit at a pressure only sufficient to overcome pressure drop through downstream processing equipment, e.g. below 100 psig, and a WHSV of 1 to 200.

In U.S. Pat. No. 4,312,790 and Re. 31,919 to Butter et al., a zeolite is incorporated with noble metal subsequent to zeolite crystallization but prior to catalyst extrusion. The catalyst is used for xylene isomerization at a temperature of 500° F. (260° C.) to 1000° F. (540° C.), a pressure between 50 and 1000 psig, a WHSV of 1 to 50 and a hydrogen/hydrocarbon male ratio of 1 to 20.

Conversion of oxygenates to hydrocarbons

U.S. Pat. No. 4,476,330 to Kerr et al., herein incorporated by reference, describes the conversion of aliphatic oxygenates to a higher molecular weight compound by contacting with a zeolite having a silica/alumina ratio substantially greater than 10 at a temperature of 70° F. (21° C.) to 1400° F. (760° C.). The feeds include lower aliphatic organic oxygenates up to $C_6$, acetals, ketals, acid halides, alcohols, carboxylic acids, aldehydes, acid anhydrides, epoxides, ethers, esters, hemiacetals, gem diols, hydroxy acids, ketones, ketenes, lactones, peracids, peroxides, sugars, and especially alcohols, ethers and esters.

Oligomerization of olefins

The modified catalysts of the invention are advantageously used in the oligomerization of olefins to form gasoline, distillate, lube oils or chemicals in conversion reactions of the type described, for example, in U.S. Pat. Nos. 4,517,399, 4,520,221, 4,547,609 and 4,547,613 which are herein incorporated by reference.

U.S. Pat. No. 4,517,399 to Chester et al. describes the conversion of olefins of 3 to 18 carbons, e.g. propylene, to high viscosity, low pour point lubricating oils by contacting with ZSM-5 type zeolites having large crystals of at least two microns. The conversion conditions include a temperature of 350° F. (177° C.) to 650° F. (343° C.) a pressure of 100 to 5000 psig, and a WHSV of 0.1 to 10.

U.S. Pat. No. 4,520,221 to Chen describes the polymerization of olefins of 2 to 8 carbons, e.g. propylene, butylene, to high viscosity lubes, e.g. linear hydrocarbons, over highly siliceous, acidic ZSM-5 type catalysts with surface acidity inactivated by treatment with base, e.g. bulky amines with a cross-section larger than about 5 Angstroms. The conversion involves a one or two stage process with the polymerization of lower olefins to linear materials, e.g. at about 200° C. over a surface poisoned zeolite, and oligomerization of the product over a modified or unmodified catalyst at a temperature of 50°–75° lower than the first stage, e.g. 150° C. Therefore, the temperatures range from 25° C. to 400° C., with a pressure of atmospheric to 1500 psi and a WHSV of 0.04 to 1.0.

U.S. Pat. No. 4,547,609 to Dessau describes a two stage process whereby in the first stage, light olefins of 2 to 6 carbons are oligomerized to gasoline and distillate liquids including aliphatics of 10 to 20 carbons over a zeolite having a crystal size greater than 0.5 micron at conditions including at a temperature of 500° F. (260° C.), or higher, e.g. a range of 500° F. (260° C.) to 800° F. (437° C.), a pressure of atmospheric to 2000 psig and a WHSV of 0.1 to 20. In the second stage, the distillate fraction is converted to high viscosity lubes by contact with a zeolite of smaller crystal size under milder conditions of a temperature about 200° F. (100° C.) to 500° F. (260° C.), a pressure of atmospheric to 650 psig, and a WHSV less than one.

U.S. Pat. No. 4,547,613 to Garwood et al. describes converting olefins of 2 to 16 carbons to high viscosity lube oil. A ZSM-5 type catalyst is preconditioned by contact with light olefins of 2 to 16 carbons, e.g. propylene at 400° F. (204° C.) to 1000° F. (538° C.), at a pressure of 0 to 100 psig for 1 to 70 hours. Conversion conditions include a temperature of 350° F. (177° C.) to 650° F. (343° C.), a pressure of 400 to 5000 psig and a WHSV of 0.1 to 10. The lube fraction may be subjected to a hydrogenation step to stabilize.

Conversion of aromatics to dialkyl-substituted benzene

The modified zeolite catalysts of the invention are advantageously used in the conversion of aromatics compounds to provide dialkyl-substituted benzene products which are highly enriched in the para-dialkyl substituted benzene isomer. Conversion reactions of this type include aromatics alkylation, transalkylation and disproportionation. Aromatics alkylations in which the catalysts of the invention can be used are described, for example, in U.S. Pat. Nos. 3,755,483, 4,086,287, 4,117,024 and 4,117,026 which are herein incorporated by reference.

As described in U.S. Pat. No. 3,755,483 to Burress, aromatic hydrocarbons such as benzenes, naphthalenes, anthracenes and substituted derivatives thereof, e.g. toluene and xylene, may be alkylated with alkylating agents such as olefins ethylene, propylene, dodecene, and formaldehyde, alkyl halides, and alkyl alcohols with 1 to 24 carbons under vapor phase conditions including a reactor inlet temperature up to about 900° F. (482° C.), with a reactor bed temperature up to about 1050° F. (566° ), at a pressure of about atmospheric to about 3000 psig, a ratio of aromatic/alkylating agent of about 1:1 to about 20:1 and a WHSV of 20 to 3000 over ZSM-12.

As described in U.S. Pat. No. 4,086,287 to Kaeding et al., monoalkylbenzenes having alkyls of 1–2 carbons, such as toluene and ethylbenzene, may be ethylated to produce a para-ethyl derivative, e.g. para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by precoking or combining with oxides of phosphorus, boron or antimony to attain a catalyst with a xylene sorption capacity greater than 1 g/100 g of zeolite and an orthoxylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psig, with hydrogen/ethylene ratio of 0.5 to 10 to reduce ageing of the catalyst. The zeolite described in U.S. Pat. No. 4,117,024 has a crystal size greater then one micron, and is modified as the catalyst in U.S. Pat. No.4,086,287 to attain the sorption capacity described in U.S. Pat. No. 4,086,287.

U.S. Pat. No. 4,117,026 to Haag and Olson describes the production of para-dialkyl benzenes having alkyls of 1 to 4 carbons under conditions which vary according to the feed. When the feed includes monoalkyl substituted benzenes having an alkyl of 1 to 4 carbons, olefins of 2 to 15, or paraffins of 3 to 60 carbons or mixtures thereof, conversion conditions include a temperature of 250° C. to 750° , a pressure of 0.1 to 100 atmospheres and a WHSV of 0.1 to 2000. For the disproportionation of toluene, the conditions include a temperature of 400° C. to 700° C., a pressure of 1 to 100 atmospheres and a WHSV of 1–50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C., a pressure of 1 to 100 atmospheres and a WHSV of 0.1 to 100. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions includes a temperature of 250° C. to 500° C. and a pressure greater than 200 psig. In the absence of added aromatics, the olefins and higher paraffins are more reactive and require lower severity of operation, e.g. a temperature of 250° C. to 600° C., preferably 300°–550° C. The catalyst described in U.S. Pat. No. 4,117,026 is modified as in U.S. Pat. No. 4,086,287.

Conversion of light paraffins and olefins to aromatics

The modified catalysts of the invention may also be used in the conversion of light paraffins and olefins to aromatics in processes of the type described, for example, in U.S. Pat. Nos. 3,760,024 and 3,756,942 which are herein incorporated by reference.

U.S. Pat. No. 3,760,024 to Cattanach describes a process for the conversion of paraffins of 2 to 4 carbons and/or olefins to aromatics of 6 to 10 carbons over a ZSM-5 type catalyst with or without hydrogenation/dehydrogenation component. Conversion conditions include a temperature of 100° C. to 650° C., a pressure of 0 to 1,000 psig, a WHSV of 0.1 to 500 and a hydrogen/hydrocarbon ratio of 0 to 20.

U.S. Pat. No. 3,756,942 to Cattanach describes the conversion of paraffins, olefins and naphthenes to aromatics over ZSM-5 type catalysts. If the feed contains at least 35 wt. % olefins, conversion is at 650° F. (363° C.) to 1400° F. (760° C.). If the feed contains less than 35 wt. % olefins, the temperature is 900° F. (482° C.) to 1400° F. (760° C.) with the absence of substantial added hydrogen. For both types of feed, the pressure is atmospheric to 35 atmospheres and the WHSV 1 to 15.

Pyridine synthesis

The modified catalysts of the invention are also advantageously used in the synthesis of pyridine. Pyridine bases may be produced through the reactions of aldehydes and ketones with ammonia. The reaction of acetaldehyde with ammonia in the presence of heterogenous catalysts at about 350° C. to about 550° C. yields 2-and 4-methylpyridine. Acetaldehyde, formaldehyde and ammonia react to yield pyridine and 3-methylpyridine. Pyridine synthesis is described, for example, in U.S. Pat. No. 4,675,410 to Feitler and U.S. Pat. No. 4,220,783 to Chang et al. which are herein incorporated by reference.

Caprolactam synthesis

Caprolactam is used in the commercial production of nylon. Caprolactam may be produced by Beckmann rearrangement of cyclohexane oxime over acid catalysts including zeolites. The synthesis of caprolactam is described, for example, in U.S. Pat. No. 4,359,421 which is herein incorporated by reference.

Therefore, the modified catalysts of the present invention are suitable for use in a variety of shape selective hydrocarbon conversion processes including as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 hr$^{-1}$ to about 20 hr$^{-1}$; dehydrogenating hydrocarbon compounds with reaction conditions including a temperature of from about 300° C. to about 700° C., a pressure of from about 0.1 atmosphere to about 10 atmospheres and weight hourly space velocity of from about 0.1 to about 20; converting paraffins to aromatics with reaction conditions including a temperature of from about 300° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylene, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g. benzene and alkylbenzenes in the presence of an alkylating agent, e.g. olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylkating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

In general, therefore, catalytic conversion conditions over a catalyst comprising the modified zeolite include a temperature of from about 100° C. to about 760° C., a pressure of from about 0.1 atmosphere (bar) to about 200 atmospheres (bar), a weight hourly space velocity of from about 0.08 hr$^{-1}$ to about 2000 hr$^{-1}$ and a hydrogen/organic, e.g. hydrocarbon compound of from 0 to about 100.

Toluene Disproportionation

Toluene Disproportionation is representative of shape selective conversions. Though the methylation reaction of the present invention is described herein in terms of disproportionation, the present invention also applies to other methylation reactions such as those using methylhalides and methylethers. Normally a single pass conversion of a toluene stream results in a product stream which includes dimethylbenzenes having alkyl groups at all locations, i.e., ortho-, meta-, and para-xylenes. Furthermore, the xylenes are known to proceed in a reaction which produces unwanted ethylbenzenes (EB) by the following reaction:

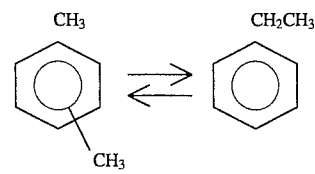

Until the present invention, the yield of p-xylene in a single pass has been limited by thermodynamics to approximately 8.2% when isomerization is permitted. This efficiency is reduced somewhat by the production of ethylbenzene.

The present invention, however, provides high efficiency conversion which reduces production of ortho- and meta-isomers to the benefit of the desired para-isomer. The resulting product stream preferably contains a para-xylene purity of at least 94%, more preferably at least 95%, and most preferably at least 97%. For example, the ortho-xylene isomer can be reduced to not more than about 0.5% of the total xylene content while the meta-xylene isomer can be reduced to less than about 5% of the total xylene content. Moreover, when the reaction system is properly treated, such as by deposition of platinum on the molecular sieve, the presence of ethylbenzene can be significantly reduced, e.g., to less than about 2% of the $C_8$ product. Other additives which may be used to reduce the production of ethylbenzene have been set forth hereinafter.

Included in the present invention is a process for the selective disproportionation of a toluene feedstock into para-xylene utilizing a high-efficiency para-xylene selectivating agent. The selectivating agent advantageously increases the para-selectivity of the catalyst and, therefore, the efficiency of para-xylene production during the conversion of toluene to xylene. As used herein, the term "high efficiency, p-xylene selectivating agent" is used to indicate substances which will increase the para-selectivity of a catalytic molecular sieve to the stated levels while maintaining commercially acceptable toluene to xylene conversion levels. Such substances include volatile organosilicon compounds with sufficient vapor pressure for proper deposition under conversion conditions, i.e., temperature ranging from about 100° C. to about 600° C., preferably from about 300° C. to about 500° C.; pressures ranging from about 0 to about 2000 psig, preferably from about 15 to about 800 psig; a mole ratio of hydrogen to hydrocarbons from about 0 (i.e. no hydrogen is present) to about 10, preferably from about 1 to about 4; at a weight hourly space velocity (WHSV) from about 0.1 to about 100 hr$^{-1}$, preferably from about 0.1 to about 10 hr$^{-1}$. It is preferred that the organosilicon compound have a kinetic diameter greater than that of the largest pore of the zeolite. Upon thermolysis, a siliceous coating is deposited on the zeolite surface, eliminating surface activity and enhancing shape-selectivity.

The volatile organosilicon compounds comprise polysiloxanes including silicones, and also siloxanes, and silanes including disilanes and alkoxysilanes.

Silicone compounds which can be used in the present invention can be characterized by the general formula.:

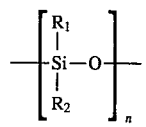

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between about 80 and about 20,000 and preferably within the approximate range of 150 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropysilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenylcyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethylcyclopentasiloxane, hexamethyldisiloxane, octamethytrisiloxane, decamethyltetrasiloxane, hexaethylcyclotrisiloxane, octaethylcyclotetrasiloxane, hexaphenylcyclotrisiloxane and octaphenylcyclotetrasiloxane.

Useful silanes, disilanes or alkoxysilanes include organic substituted silanes having the general formula:

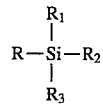

wherein R is a reactive group such as hydrogen, alkoxy, halogen, carboxy, amino, acetamide, trialkylsilyl. $R_1$, $R_2$ and $R_3$ can be the same as R or an organic radical which may include alkyl of from 1 up to about 40 carbon atoms, alkyl or aryl carboxylic acid wherein the organic portion of the alkyl contains about 1 to 30 carbon atoms and the aryl group contains about 6 to 24 carbon atoms, aryl groups of about 6 to 24 carbons which may be further substituted, alkylaryl and arylalkyl groups containing about 7 up to about 30 carbon atoms. Preferably, the alkyl group of an alkyl silane is between 1 and 4 carbon atoms in chain length. Mixtures may also be used.

The silanes or disilanes include, as non-limiting examples, dimethylphenylsilane, phenytrimethylsilane, triethylsilane and hexamethyldisilane. Useful alkoxysilanes are those with at least one silicon-hydrogen bond.

While not wishing to be bound by theory, it is believed that the advantages of the present invention are obtained by rendering acid sites on the external surfaces of the catalyst substantially inaccessible to reactants while increasing catalyst tortuosity. Acid sites existing on the external surface of the catalyst are believed to isomerize the para-xylene exiting the catalyst pores back to an equilibrium level with the other two isomers thereby reducing the amount of para-xylene in the xylenes to only about 24%. By reducing the availability of these acid sites to the para-xylene exiting the pores of the catalyst, the relatively high level of para-xylene can be maintained. It is believed that the high-efficiency, p-xylene selectivity agents of the present invention block or otherwise render these external acid sites unavailable to the para-xylene by chemically modifying said sites.

Preferably, the kinetic diameter of the high efficiency, p-xylene selectivating agent is larger than the zeolite pore diameter, in order to avoid reducing the internal activity of the catalyst.

In line with this theory, it is also believed that the presence of hydrogen in the reaction zone is important in order to maintain the desired high yields of para-xylene when a silicone compound is used as the high-efficiency para-xylene selectivating agent. The importance of the hydrogen in the feedstock may be reduced in alternative embodiments by using a high efficiency para-xylene selectivating agent comprising silane or some other compound which effectively renders the isomerizing acid sites on the external surface of the catalyst inaccessible.

One process of the present invention utilizes a high-efficiency para-xylene selectivating agent comprising a silicon compound wherein the silicon compound is introduced by co-feeding, for example, at least one silicon compound with the toluene feedstock over a conversion catalyst at reaction conditions.

The toluene feedstock preferably comprises about 50% to 100% toluene, more preferably at least about 80% toluene in the toluene feedstock. Other compounds such as benzene, xylenes, and trimethylbenzenes may also be present in the toluene feedstock without adversely affecting the present invention.

According to the processes of this invention, the toluene feedstock may also be dried, if desired, in a manner which will minimize moisture entering the reaction zone. Methods known in the art suitable for drying the toluene charge for the present process are numerous. These methods include percolation through any suitable dessicant, for example, silica gel, activated alumina, molecular sieves or other suitable substances, or the use of liquid charge dryers.

The catalytic molecular sieves of the present invention are in the hydrogen form and preferably comprise an intermediate pore-size zeolite such as a ZSM-5, ZSM-11, ZSM-22, ZSM-23, or ZSM-35. The catalyst of the present invention preferably has an alpha value greater than 100, for example about 150–2000, and a silica-alumina ratio less than 100, preferably about 20–80. The Alpha Value of the catalyst may be increased by treating the catalyst with nitric acid or by mild steaming as discussed in U.S. Pat. No. 4,326,994.

The Alpha Value is an approximate indication of the catalytic cracking activity of the catalyst compared to a standard catalyst and it gives the relative rate constant (rate of normal hexane conversion per volume of catalyst per unit time.) It is based on the activity of an amorphous silica-alumina cracking catalyst taken as an Alpha of 1 (Rate Constant=0.016 sec$^{-1}$). The Alpha Test is described in U.S. Pat. No. 3,354,078 and in The Journal of catalysis, vol. 4, pp. 522–529 (August 1965): Vol. 6, p. 278 (1966); and Vol. 61, p. 395 (1980), each incorporated herein by reference as to that description. It is noted that intrinsic rate constants for many acid-catalyzed reactions are proportional to the Alpha Value for a particular crystalline silicate catalyst (see "The Active Site of Acidic Aluminosilicate catalysts," *Nature*, Vol. 309, No. 5959, pp. 589–591, Jun. 14, 1984). The experimental conditions of the test used herein include a constant temperature of 538° C. and a variable flow rate as described in detail in the *Journal of Catalysis*, Vol. 61, p. 395. The catalytic molecular sieves also preferably have an initial Constraint Index of about 1–12. The method by which Constraint Index is determined is described fully in U.S. Pat. No. 4,016,218, incorporated herein by reference for details of the method. The crystal size of zeolites used herein is preferably greater than 0.1 micron.

For the improved disproportionation process of this invention, the suitable molecular sieve may be employed in combination with a support or binder material such as, for example, a porous inorganic oxide support or a clay binder. The preferred binder is primarily silica. Other non-limiting examples of binder materials include alumina, zirconia, magnesia, thoria, titania, boria and combinations thereof, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be about 30 to about 90 percent by weight and is preferably about 50–80 percent by weight of the composition. The composition may-be in the form of an extrudate, beads, or fluidizable microspheres.

Operating conditions employed in the improved process of the present invention will affect the reaction rate, para-selectivity, and conversion. Such conditions include the temperature, pressure, space velocity, and the hydrogen to hydrocarbon mole ratio. One preferred embodiment of the present invention comprises contacting a catalytic molecular sieve with a toluene feedstock which includes a silicone compound under conditions for effecting vapor-phase disproportionation. Conditions effective for accomplishing the high para-selectivity and acceptable toluene disproportionation conversion rates include a reactor inlet temperature of about 350°–540° C., preferably greater than about 400° C., a pressure of about atmospheric—5000 psig, preferably about 100 to 1000 psig, a WHSV of about 0.1–20, preferably about 2–4, and a hydrogen to hydrocarbon mole ratio of about 0.1–20, preferably about 2–4. This process may be conducted in either fixed- or fluid-bed mode with attendant benefits of either operation readily obtainable.

The effluent is separated and distilled to remove the desired product, i.e., para-xylene, plus other by-products. The unreacted reactant, i.e. toluene, is preferably recycled for further reaction. The benzene is a valuable co-product.

In accordance with another embodiment of the present invention, the catalyst is further modified in order to reduce the amount of undesirable by-products, particularly ethylbenzene. The state of the art is such that the reactor effluent from toluene disproportionation typically contains about 0.5% ethylbenzene by-product. Upon distillation of the reaction products, the level of ethylbenzene in the $C_8$ fraction often increases to about 3–4 percent. This level of ethylbenzene is unacceptable for polymer grade p-xylene since ethylbenzene in the $C_8$ product, if not removed, degrades the quality of fibers ultimately produced from the p-xylene product. Consequently, ethylbenzene content must be kept low. The specification for ethylbenzene in the $C_8$ product has been determined by industry to be less than 0.3%. The ethylbenzene can be substantially removed by isomerization or by superfractionation processes. Removal of the ethylbenzene by conventional isomerization would be impractical with the present invention since the xylene stream, which advantageously comprises greater than 85% para-xylene, would be concurrently isomerized to equilibrium xylenes reducing the amount of para-xylene in this xylene Stream to about 24%. And it is known that the alternative procedure of removing the ethylbenzene by superfractionation is extremely expensive.

In order to avoid the need for downstream ethylbenzene removal, the level of ethylbenzene by-product is advantageously reduced by incorporating a hydrogenation-dehydrogenation function in the catalyst via addition of a metal compound such as platinum. While platinum is the preferred metal, other metals such as palladium, nickel, Copper, cobalt, molybdenum, rhodium, ruthenium, silver, gold, mercury, osmium, iron, zinc, cadmium, and mixtures thereof may be utilized. The metal may be added by cation exchange, in amounts of about 0.01–2%, typically about 0.5%. The metal must be able to enter the pores of the catalyst in order to survive a subsequent calcination step. For example, a platinum modified catalyst can be prepared by first adding to the catalyst a solution of ammonium nitrate in order to convert the catalyst to the ammonium form, and subsequently, an aqueous solution of tetraamine platinum(II) nitrate to increase activity. The catalyst can then be filtered, washed with water and calcined at temperatures of about 250° to 500° C.

By the present process, toluene is converted to aromatic concentrates of high value, e.g., over 90% para-xylene and benzene. In a typical embodiment of the present process, toluene conversion is found to be about 20–25% with a para-xylene selectivity of about 85%–97% based on the $C_8$ product. Para-xylene selectivity in these high percentages and at these commercially acceptable toluene conversion levels provides a significant improvement over previously used processes.

The following examples will serve to further illustrate processes and some advantages of the present invention.

EXAMPLE 1

Toluene disproportionation with Trim Selectivation was carried out in a fixed-bed reactor using 2 grams of a silica bound HZSM-5 catalyst having a silica/alumina ratio of 26, a crystal size of 0.1 micron, an Alpha Value of 731, and 1% silicone compound having a phenylmethyl silicon to dimethyl silicon ratio of 1:1 in a toluene feed. Operating conditions were 4.0 WHSV, 480° C., psig, and a hydrogen/hydrocarbon ratio of 2. Table 1 summarizes toluene conversion and para-xylene selectivity as a function of time on stream during and after trim selectivation.

TABLE 1

| Time on Stream, hr | Conversion, wt % | para-Xylene in Xylenes, wt % |
| --- | --- | --- |
| 1 | 56 | 22 |
| 6 | 57 | 21 |
| 22 | 51 | 24 |
| 46 | 42 | 39 |
| 98 | 36 | 70 |
| 143 | 28 | 86 |
| 170 | 25 | 89 |
| 174* | 25 | 91 |
| 342* | 25 | 91 |

*Silicone co-feed discontinued.

It is noteworthy that the silicone trim selectivation substantially increased para-xylene selectivity from an initial 22% to 89%. At 174 hours on stream the feed was changed to 100% toluene, i.e., the silicone co-feed was discontinued. Over the following one week test period, toluene conversion remained constant at 25% and para-xylene selectivity remained constant at 91%.

EXAMPLE 2

Toluene disproportionation with Trim Selectivation of 2 grams of Silica bound HZSM-5 was carried out at 4.0 WHSV, 446° C., 500 psig, and a hydrogen/hydrocarbon ratio=2. Table 2 summarizes toluene conversion and para-xylene selectivity as a function of time on stream.

TABLE 2

| Time on Stream, hr | Conversion, wt % | p-Xylene in Xylenes, wt % |
|---|---|---|
| 1 | 44 | 29 |
| 25 | 42 | 34 |
| 47 | 37 | 58 |
| 94 | 31 | 86 |
| 143 | 29 | 93 |
| 176 | 27 | 96 |
| 199 | 26 | 97 |
| 223 | 25 | 97 |
| 239* | 25 | 97 |

*Silicone co-feed discontinued.

Silicone selectivation increased para-xylene selectivity from 24% (thermodynamic value) to a high 97% at 25% toluene conversion. When the silicone co-feed was discontinued, the para-xylene selectivity and toluene conversion were unchanged at 97% and 25%, respectively.

EXAMPLE 3

Toluene disproportionation with Trim Selectivation of 2 g of a silica bound HZSM-5 was also carried out at 4.0 WHSV, 420° C., 0 psig, and hydrogen/hydrocarbon ratio=0. Table 3 summarizes toluene conversion and para-xylene selectivity as a function of time on stream. Note that the conversion drops to essentially zero at 184 hours on stream in contrast to operation in the presence of hydrogen where at 184 hours on stream conversion has stabilized at 25%.

TABLE 3

| Time on Stream, hr | Conversion, wt % | para-xylene in Xylenes, wt % |
|---|---|---|
| 1 | 14 | 27 |
| 48 | 8 | 51 |
| 96 | 2 | 82 |
| 136 | 1 | 93 |
| 184 | 0.1 | 97 |

Figure 2:
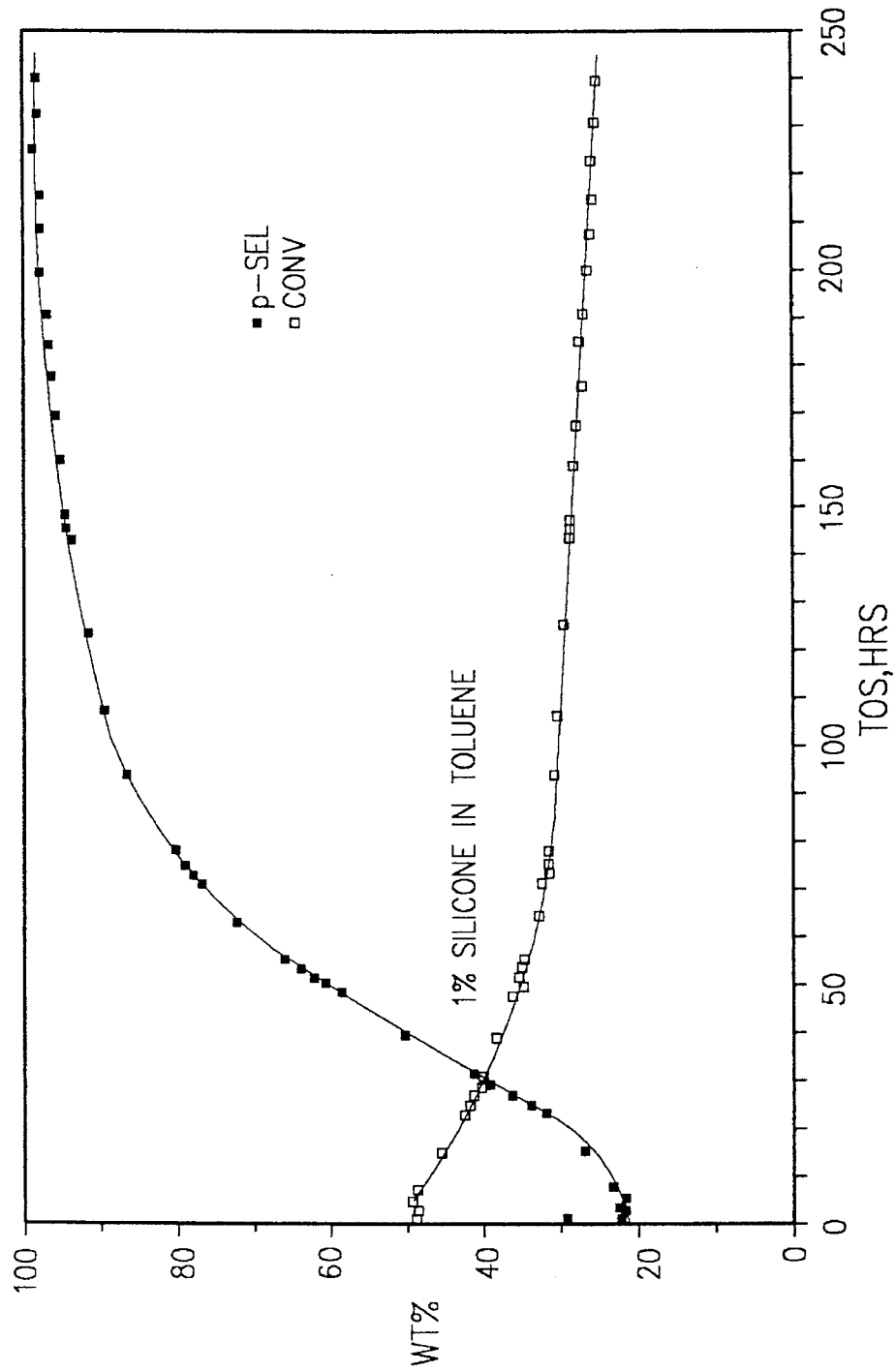
FIG. 2 is a graph similar to FIG. 1 and provides results of a hydrogen co-feed at a slightly lower temperature.
Figure 3:
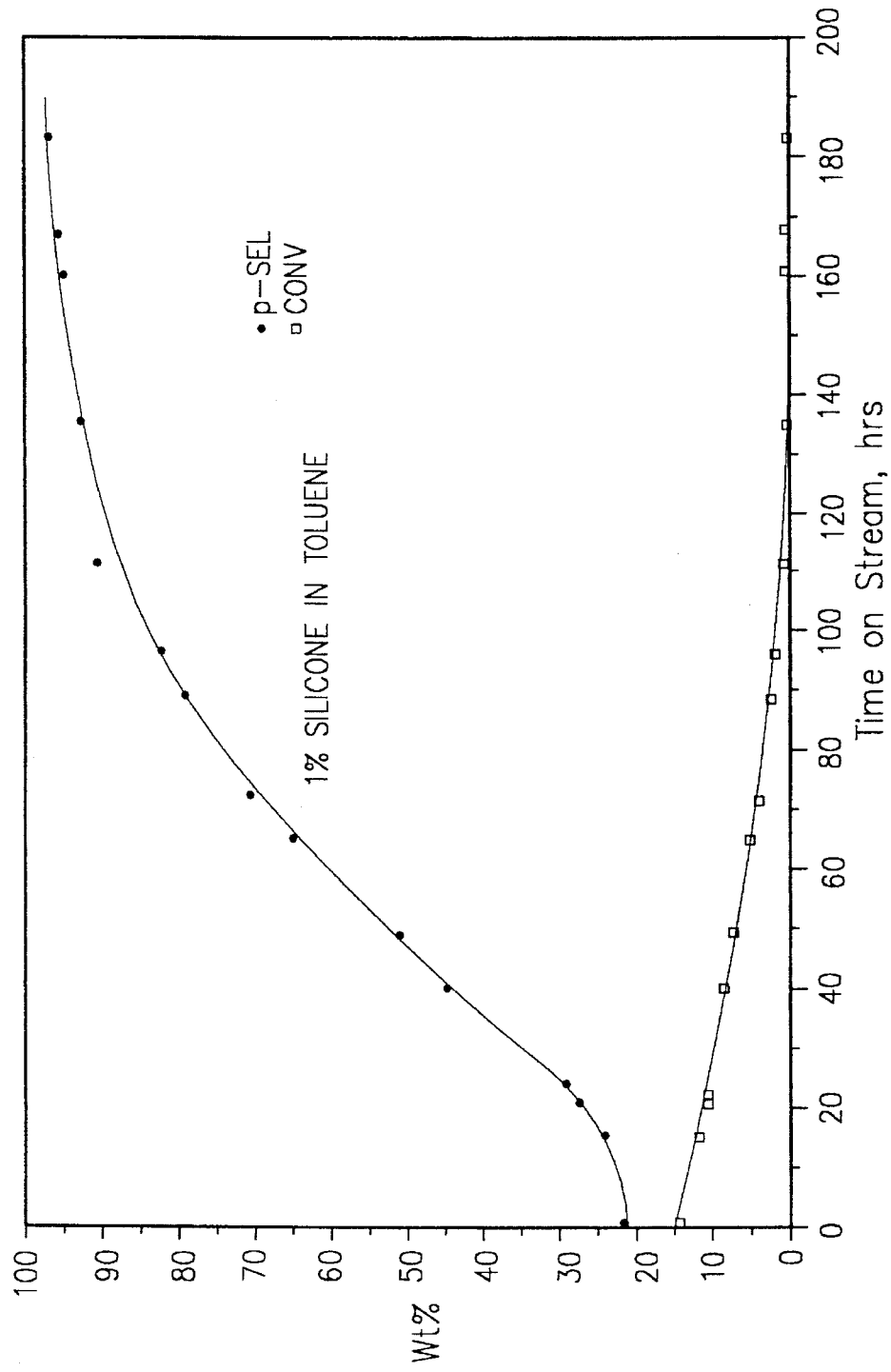
FIG. 3 is also a graph similar to FIG. 1 and shows results obtained in the absence of a hydrogen co-feed.

FIGS. 1 to 3 illustrate the benefits of including hydrogen in the feedstock when the high efficiency, p-xylene selectivating agent is a silicone compound. FIG. 1 provides a comparison between the uses of hydrogen and nitrogen during the selectivation of a ZSM-5 catalyst with phenylmethyl silicone. During this reaction, a toluene feedstock comprising 1% phenylmethyl silicone and hydrogen or nitrogen in an amount equal to a subject gas to hydrocarbon ratio of 2, was fed over the catalyst at 480° C., at a pressure of 500 PSIG and at WHSV of 4. The para-selectivity of the reaction in the presence of hydrogen gas increased steadily to a level of about 90% at a toluene-to-xylene conversion of about 25%. As indicated in Table 1, the para-selectivity and conversion continued at high levels even after the feedstock was changed to 100% toluene after about 170 hours on stream. In the presence of nitrogen, on the other hand, the catalyst deactivated rapidly and conversion quickly approached zero. The results of Table 1 therefore indicate that the use of nitrogen with a silicone selectivating agent in the absence of hydrogen fails to provide the advantages of the present invention.

FIG. 2 is a similar graph showing both the para-selectivity and toluene conversion but at a temperature of 446° C., a pressure of 500 PSIG, a WHSV of 4, and a hydrogen/hydrocarbon ratio of 2. Table 2 indicates that stable operation was attained at 25% conversion with high 97% p-xylene.

FIG. 3 supports the conclusion that the use of a silicone compound in combination with hydrogen in the feedstock provides the advantageous results of the present invention. FIG. 3 shows the results of an experiment wherein the feedstock contained 1% phenylmethyl silicone but no hydrogen. The toluene conversion rate steadily approached zero.

A 1% solution of silicone in toluene need not be optimal, i.e., a more rapid selectivation may occur with a 5% solution. Also, although a silicone containing phenylmethylsilicon and dimethylsilicon groups was used in this study, other silicon and organosilicon compounds may be effective in increasing the para-selectivity of the disproportionation reaction.

The spent catalyst can be regenerated by methods known in the art, such as by air regeneration. Thereafter, the catalyst can once again be trim selectivated and reused.

EXAMPLE 4

Toluene Disproportionation with Trim Selectivation of $SiO_2$-HZSM-5 was carried out using 1% octamethylcyclotetrasiloxane in toluene feed. Operating conditions were 446° C., 500 psig, 4.0 WHSV, and $H_2$/HC=2. Table 4 summarizes the results.

TABLE 4

| Time on Stream, Hrs. | p-Xylene/ Xylenes, wt % | Toluene Conversion, wt % |
|---|---|---|
| 0 | 25 | 40 |
| 24 | 88 | 23 |
| 46 | 95 | 18 |
| 71 | 98 | 15 |

EXAMPLE 5

Toluene disproportionation with Trim Selectivation as in Example 4 was carried out using hexamethyldisiloxane. Table 5 and FIG. 4 summarize the results.

TABLE 5

| Time on Streams, hrs. | p-Xylene in Xylenes, wt % | Toluene Conversion, wt % |
|---|---|---|
| 1 | 28 | 47 |
| 2 | 56 | 42 |
| 4 | 80 | 37 |
| 14 | 95 | 33 |
| 24 | 98 | 28 |
| 47 | 99 | 20 |
| 54 | 99 | 18 |

FIG. 4 illustrates the high p-xylene selectivity and toluene conversion over 350 hours on stream. The toluene conversion remained at about 18–20% with a p-xylene selectivity of 99% for an extended period Of time. HMDS was discontinued at about 50 hours.

EXAMPLES 6–14

Toluene disproportionations with Trim, Selectivations as in Examples 4 and 5 were carried out with the siloxanes listed in Table 6. Operating conditions were 446° C., 500 psig, 4.0 WHSV and $H_2/HC=2$. The results after 24 hours are shown in Table 6.

TABLE 6

| Ex. | Siloxanes | p-Xylene/Xylenes, wt. % | Toluene Conversion wt. % |
|---|---|---|---|
| 6 | Methylhydrocyclosiloxanes | 89 | 13 |
| 7 | Hexamethylcyclotrisiloxane | 84[a] | 20 |
| 8 | 1,3,5-Trimethyl-1,3,5-triphenylcyclotrisiloxane | 85 | 31 |
| 9 | Octamethylcyclotetrasiloxane | 88 | 23 |
| 10 | Decamethylcyclopentasiloxane | 90 | 28 |
| 11 | Decamethyltetrasiloxane | 98 | 24 |
| 12 | Hexamethyldisiloxane | 98 | 24 |
| 13 | 1,1,3,3,5,5-Hexamethyltrisiloxane | 96 | 14 |
| 14 | Octamethyltrisiloxane | 81 | 20 |

[a] 41 hours on stream

Continuation of the trim selectivation beyond these time periods brings the p-xylene selectivity to above 90% with toluene conversion of at least 15% in these examples.

EXAMPLES 15–19

Trim Selectivations as in Examples 4 and 5 were carried out with the silanes listed in Table 7. Operating conditions were 446° C., 500 psig, 4.0 WHSV and $H_2/HC=2$. The results after 24 hours are shown in Table 7.

TABLE 7

| Ex. | Siloxanes | p-Xylene/Xylenes, wt. % | Toluene Conversion wt. % |
|---|---|---|---|
| 15 | Diphenylsilane | 96 | 15 |
| 16 | Dimethylphenylsilane | 97 | 19 |
| 17 | Phenyltrimethylsilane | 86 | 19 |
| 18 | Triethylsilane | 85 | 21 |
| 19 | Hexamethyldisilane | 95 | 23 |

Continuation of the trim selectivation beyond 24 hours brings the p-xylene selectivity to above 90% in these examples.

EXAMPLES 20–24

For comparison purposes, the compounds listed in Table 8 were tested as in Examples 6–19 with results shown in Table 8.

TABLE 8

| Ex. | Siloxanes | p-Xylene/Xylenes, wt. % | Toluene Conversion wt. % |
|---|---|---|---|
| 20 | Hexaphenylcyclotrisiloxane | 43 | 29 |
| 21 | Octaphenylcyclotetrasiloxane | 66 | 28 |
| 22 | Tetra-(n-butyl)-orthosilicate | 36 | 2 |
| 23 | Tetra-ethyl-orthosilicate | 38 | 3 |
| 24 | Tetra-(2-ethylhexyl)-orthosilicate | 33 | 1 |

EXAMPLE 25

Toluene alkylation with ethylene was carried out at 468° C. and 100 psig over 1.0g $SiO_2$-HZSM-5 catalyst trim selectivated using 1% phenylmethyl silicone in toluene at 446° C., 500 psig, 4 WHSV, and $H_2/HJC=2$. Toluene was pumped at 4 WHSV. Ethylene and hydrogen were cofed to maintain the mole ratio toluene/ethylene/hydrogen=8/1/3. At 10% toluene conversion (80% of the 12.5% theoretical maximum conversion), the selectivity to p-ethyltoluene was a very high 99.1% with only 0.9% m-ethyltoluene.

EXAMPLE 26

Toluene alkylation with methanol was carried out at 448° C. and 500 psig over 2.00g $SiO_2$-HZSM-5 catalyst trim selectivated as described above. Toluene was pumped at 4 WHSV. Methanol and hydrogen were cofed to maintain the mole ratio toluene/methanol/hydrogen=4/1/8. At 14% toluene conversion (56% of the theoretical 25% maximum conversion), the selectivity to p-xylene was a very high 99.9% with only 0.1% m-xylene.

EXAMPLE 27

Conversion of n-heptane was carried out 446° C., 0 psig, and 4 WHSV over 2.00g $SiO_2$-HZSM-5 catalyst trim selectivated as described above. The aromatic product distribution at 21% heptane conversion is shown in the following table. The p-xylene selectivity in the xylene fraction was a very high 99.3% with only 0.7% m-xylene.

| Component | Wt. % |
|---|---|
| Benzene | 6.2 |
| Toluene | 44.6 |
| Ethylbenzene | 4.7 |
| Xylenes | 39.5 |
| p-Ethyltoluene | 5.0 |
| | 100.0 |

EXAMPLE 28

Conversion of methanol was carried out at 371° C., psig, and 1 WHSV over 1.00 g $SiO_2$-HZSM-5 catalyst trim selectivated as described above. The liquid product distribution at 100% methanol conversion is shown in the following table

| Component | Wt. % |
|---|---|
| $C_5$–$C_6$ | 2.0 |
| Benzene | 7.3 |
| Toluene | 84.0 |
| Ethylbenzene | 2.2 |
| Xylenes | 42.1 |
| $C_{9+}$ | 12.4 |
| | 100.0 |

EXAMPLE 29

A Fries reaction of phenylacetate is carried out at 400° C., 100 psig, and 1 WHSV over $SiO_2$-HZSM-5 catalyst trim selectivated as described above. The 4-hydroxyacetophenone product is obtained in high selectivity.

EXAMPLE 30

Propylene oligomerization is carried out at 200° C., 600 psig, and 0.25 WHSV over $SiO_2$-HZSM-5 catalyst trim selectivated as described above. The diesel and lube products are obtained with high selectivity to the desirable straight chain hydrocarbons.

EXAMPLE 31

Distillate dewaxing is carried out at 650° F., 400 psig, and 1 WHSV over $SiO_2$-HZSM-5 catalyst trim selectivated as described above. The product quality is substantially improved by the selective Cracking of straight chain, waxy hydrocarbons. The pour point of a heavy gas oil improves from 95° F. to 20° F. while the cloud point improves from 96° F. to 20° F.

What is claimed is:

1. A catalyst for shape selective hydrocarbon conversions comprising:

a catalytic intermediate pore molecular sieve having a Constraint Index of about 1–30 which has been trim selectivated by contact with a mixture of a high-efficiency, para-xylene selectivating agent, said agent selected from the group consisting of polysiloxanes, siloxanes, silanes, disilanes and alkoxysilanes, said mixture comprising said agent and hydrogen and toluene, at reaction conditions for converting toluene to xylene, said catalyst yielding at least about 90% para-xylene based on $C_8$ products and concurrently therewith a toluene conversion of at least about 15% in toluene disproportionation.

2. The catalyst according to claim 1 wherein said reaction conditions comprise a temperature of about 350°–540° C., a pressure of about atompsheric—5000 psig, a WHSV of about 0.1–20, and a hydrogen to hydrocarbon molar ratio of about 0.1–20.

3. The catalyst according to claim 1 wherein said catalytic molecular sieve includes a metal hydrogenation-dehydrogenation component.

4. The catalyst according to claim 3 wherein said metal comprises platinum.

5. The catalyst according to claim 3 wherein said catalytic molecular sieve comprises ZSM-5.

6. The catalyst according to claim 5 wherein said catalyst comprises a silica bound ZSM-5 with a crystal size of at least about 0.1 micron.

7. The catalyst according to claim 1 wherein said agent is a volatile organosilicon compound.

* * * * *